United States Patent
Gizurarson et al.

(10) Patent No.: US 6,514,503 B1
(45) Date of Patent: Feb. 4, 2003

(54) ANTIGEN DELIVERY SYSTEM

(75) Inventors: Sveinbjörn Gizurarson, Reykjavik (IS); Vera Gudmundsdottir, Reykjavik (IS)

(73) Assignee: Lyfjathoun HF, Reykjavik (IS)

( * ) Notice: Subject to any disclaimer, the term of this patent is extended or adjusted under 35 U.S.C. 154(b) by 0 days.

(21) Appl. No.: 09/112,684

(22) Filed: Jul. 9, 1998

(30) Foreign Application Priority Data

Jul. 9, 1997 (IS) .................................................. 4518

(51) Int. Cl.[7] ........................ A61K 45/00; A61K 47/00; A61K 39/02

(52) U.S. Cl. ............................. 424/278.1; 424/234.1; 424/184.1; 514/2

(58) Field of Search .................. 424/278.1, 234.1, 424/184.1; 514/2

(56) References Cited

U.S. PATENT DOCUMENTS

| | | | |
|---|---|---|---|
| 4,349,540 A | 9/1982 | D'Hinterland et al. | 424/92 |
| 4,420,484 A | 12/1983 | Gorman et al. | 424/326 |
| 4,567,161 A | 1/1986 | Posanski et al. | 514/23 |
| 4,610,868 A | 9/1986 | Fountain et al. | 424/1.1 |
| 4,681,900 A | 7/1987 | Iwasaki | 514/786 |
| 4,911,928 A | 3/1990 | Wallach | 424/450 |
| 5,314,685 A | * 5/1994 | Tyle et al. | |
| 5,438,040 A | * 8/1995 | Ekwuribe | 514/3 |
| 5,561,062 A | 10/1996 | Varanelli et al. | 435/238 |
| 5,633,226 A | 5/1997 | Owen et al. | 514/2 |
| 5,942,237 A | * 8/1999 | Gizuarson | |

FOREIGN PATENT DOCUMENTS

| | | |
|---|---|---|
| EP | 0 275 709 A1 | 7/1988 |
| EP | 0 324 455 A2 | 7/1989 |
| EP | 0 544 612 A2 | 6/1993 |
| EP | 0 781 559 A2 | 2/1997 |
| GB | 822718 | 10/1959 |
| JP | 309347/91 | 11/1991 |
| WO | 92/16221 | * 10/1992 |
| WO | WO 92/18147 | 10/1992 |
| WO | WO 93/21293 | 10/1993 |
| WO | WO 94/08604 | 4/1994 |
| WO | WO 94/17827 | 8/1994 |
| WO | WO 96/22109 | 7/1996 |
| WO | WO 96/24374 | 8/1996 |

OTHER PUBLICATIONS

Product Information, "Softigen 767", Huls AG Werk Witten.

Gizurarson et al., "Evaluation of Local Toxicity After Repeated Intranasal Vaccination of Guinea–Pigs", *Toxicology*, 107:61–68 (1996).

Gizurarson, et al., "Intranasal Vaccination against Influenza Using Pharmaceutical Excipients as Immunological Adjuvants", *Vaccine Research*, 5(2):69–75 (1996).

Gizurarson, et al., "Intranasal Vaccination against Influenza Using Pharmaceutical Excipients as Immunological Adjuvants", *Vaccine Research*, 5(2):69–75 (1996). (From *Chem. Abstracts*, (1996) 125(17), Abstract No. 276069).

Gizurarson et al., "Intranasal Vaccination Against Diphtheria and Tetanus in Human Subjects", *Vaccine Research*, 6(1):41–47 (1997).

Aggerbeck, et al., "Intranasal Booster Vaccination Against Diphtheria and Tetanus in Man", *Vaccine*, 15(3):307–316 (1997).

Aggerbeck, et al., "Intranasal Booster Vaccination Against Diphtheria and Tetanus in Man", *Vaccine*, 15(3):307–316 (1997). (From *Chem. Abstracts*, (1997) 126(21), Abstract No. 276069).

Frisch, Benoit, et al., "Synthesis of Short Polyoxyethylene–Based Heterobifunctional Crosslinking Reagents", *Bioconjugate Chem.*, 7(2): 180–186 (1996) (from *Chem. Abstracts*, 1996, vol. 124, No. 14, Abstract No. 185293).

Boeckler, Christophe, et al., "Immunogenicity of New Heterobifunctional Crosslinking Reagents Used in the Conjugation of Synthetic Peptides to Liposomes", *J. Immunol. Methods*, 191(1):1–10 (1996) (from *Chem. Abstracts*, vol. 125, No. 7, Abstract No. 7774).

* cited by examiner

*Primary Examiner*—Mary K. Zeman
(74) *Attorney, Agent, or Firm*—Hamilton Brook Smith & Reynolds, P.C.

(57) ABSTRACT

Adjuvants for administration, particularly for mucosal administration, of an antigen, are described, as well as compositions comprising the described adjuvant in combination with an antigen and a physiologicially acceptable vehicle. Methods of eliciting and enhancing an immune response utilizing the adjuvant compositions of the invention are also described.

28 Claims, No Drawings

ANTIGEN DELIVERY SYSTEM

RELATED APPLICATION

This application is a continuation-in-part of Icelandic patent application 4518, filed Jul. 9, 1997, the entire teachings of which are incorporated herein by reference.

BACKGROUND OF THE INVENTION

Parenteral administration (intramuscular and subcutaneous) of antigens or vaccines is normally regarded as the most effective route of administration. However, administration by injection has a number of disadvantages. Injection of an antigen or vaccine requires the use of sterile syringes and administration by trained personnel, and may cause pain and irritation, particularly in the case of repeated injections. This route of administration also poses a risk of infection. More significantly, intramuscular injections are often poorly tolerated by the individual, and may possibly cause an induration (hardening of tissue), hemorrhage (bleeding) and/or necrosis (local death of tissue) at the injection site.

The mucosal membrane contains numerous dendritic cells which are excellent antigen-presenting cells. The mucosal membranes are also connected to lymphoid organs, called mucosal-associated lymphoid tissue, which are able to potentiate an immune response to other mucosal areas. One example of such a mucosal membrane is the nasal epithelial membrane, which consists essentially of a single layer of epithelial cells (pseudostratified epithelium); the mucosal membrane is connected to two lymphoid tissues, the adenoids and the tonsils. The extensive network of blood capillaries under the nasal mucosa and the high density of T and B cells are particularly suited to provide rapid recognition of the antigen and to provide a quick immunological response.

Intranasal administration of attenuated viruses, bacteria and parasites has been attempted, along with administration through other mucosal surfaces, for particular pathogens which normally infect a host by this route. The elicitation of an immune response by these antigens through mucosal surfaces is expected in such cases, because the modified live pathogen of the vaccine is following the natural route of infection of the wild-type pathogen, creating immunity through a sub-clinical infection. Mucosal administration of immunogenic compositions is of particular interest since this route is able to stimulate locally-produced antibodies (secretory IgA antibodies) and avoids the problems caused by parenteral administration. Furthermore, mucosal administration can typically be performed by an untrained person, including the individual to be treated, and young children are typically not as averse to mucosal administration as to parenteral administration. Due to the risk associated with administration of live, attenuated, modified pathogens, it is often desirable to utilize a subunit vaccine. However, the mucosal administration of purified antigens in a subunit vaccine is normally associated with a poor immune response.

A variety of vehicle systems for the delivery of antigens have been developed. One of the problems encountered in using such vehicle systems, e.g., for intranasal or mucosal administration, is that the antigen and/or the vaccine is absorbed and degraded without recognition and, therefore, without stimulating an immunological response, partially due to the short contact-time inside the nasal cavity. A mixture of polyethylene glycol substituted caprylic/capric acid glycerides and Tween 20® has been described for use as a mucosal adjuvant (Gizurarson et al., *Toxicology* 107:61–68 (1996); Gizurarson et al., *Vaccine Research* 5:69–75 (1996); Gizurarson et al., *Vaccine Research* 6:41–47 (1997)); however, this formulation produces an uncomfortable stinging sensation in the recipient at the site of administration. Thus, there is a need for an effective formulation for mucosal administration of antigens to produce an acceptable immune response.

EP Patent No. 0544612A2 discloses a composition comprising an immunogen and a triglyceride that can be orally or nasally administered. The composition can enhance the effect of the immunogen.

In one reference (U.S. Pat. No. 4,610,868; issued Sep. 9, 1986) a lipid matrix carrier is described for parenteral administration of drugs. This system requires a lipid matrix carrier comprising a hydrophobic compound, an amphipathic compound and a bioactive agent with a globular structure with 500–100000 nm in diameter. Here the hydrophobic compound may comprise a mixture of glycerides, and the amphipathic compound may comprise a sphingolipid. Furthermore, this formulation may be administered into the nasal area. This system may not be acceptable as nasal formulation, due to the rapid clearance inside the nose and the large globular structure. Therefore, this system will be removed, into the stomach, by the cilia before the bioactive agent is released. This patent does not describe the use of the adjuvant substance according to the invention.

In JP 309347/91 (priority Nov. 25, 1991) an orally or nasally administered immunogen composition comprising an immunogen capable of immunizing mammals using an adjuvant comprising of triglycerides with $C_{6-26}$ residue of saturated or unsaturated fatty acid. The use of saturated fatty acids does not induce the immune response according to the invention, and the use of triglycerides does not give the possibilities of having one hydrophilic group able to solubilize the adjuvant or having the possibility to connect the antigen to the adjuvant.

WO 94/17827 (priority Feb. 15, 1993) describes a pharmaceutical preparation for topical administration of antigens to mammals via mucosal membranes. The adjuvant/vehicle preparation is selected from (a) polyoxyethylene sorbitan monoesters, (b) polyoxyethylene castor oil, (c) caprylic/capric glycerides, and (d) gangliosides.

SUMMARY OF THE INVENTION

The present invention provides a composition which can be used as an adjuvant for the administration of antigens and vaccines, particularly for mucosal administration. The compositions of the present invention provide enhanced adhesion of the antigen to the mucosal membrane, as well as enhanced absorption of the antigen through the mucus membrane. Use of the compositions of the invention provides the ability to elicit both a systemic (e.g., antibodies of the IgG isotype) and a local (e.g., secretory antibodies of the IgA isotype) immune response in the recipients of the composition without causing unacceptable irritation of the epithelial membrane. The compositions of the invention can also be used in plants as an adjuvant to stimulate the plant immune defense system. The invention also provides a controlled delivery system for intranasal application, which is biocompatible with the mucus membrane and which is capable of administering required amounts of antigens in small volumes.

The present invention pertains to compositions which comprise an antigen and an adjuvant containing 0.01–70% v/v of glycerides selected from the group consisting of monoglycerides, diglycerides, and mixtures thereof, said glycerides having the formula (I):

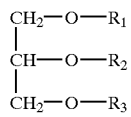

(I)

wherein $R_1$, $R_2$, and $R_3$ are independently selected from the group consisting of saturated or unsaturated $C_{6-24}$ fatty acids, water soluble polymers, and mixtures thereof, provided that the glyceride contains at least one water soluble polymer at $R_1$, $R_2$, or $R_3$. The adjuvant can also contain small amounts of triglycerides. In a particular embodiment, the water soluble polymers consist of $PEG_{2-30}$ residues of polyoxyethylene, or derivatives thereof, having 2–30 polyoxyethylene units. In another embodiment, one or two of the groups $R_1$, $R_2$, and $R_3$ are replaced by bound antigen.

In a further embodiment of the invention, the water soluble polymer is a $PEG_{3-6}$ residue of polyoxyethylene having 3 to 6 polyoxyethylene units. In another embodiment of the invention, the glycerides have a structure selected from the group consisting of:

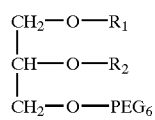

(II)

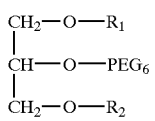

(III)

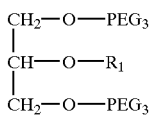

(IV)

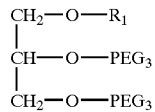

(V)

wherein in each formula, $R_1$, and $R_2$ are defined above.

In particular embodiments of the invention, $R_1$, $R_2$, and $R_3$ are selected from saturated $C_{6-4}$ fatty acids, more preferably saturated $C_{8-10}$ fatty acids.

The compositions of the invention modulate the immune response to the antigen; that is, the immunogenic or vaccine composition is capable of quantitatively and/or qualitatively improving the vaccinated host's antibody response. This can be accomplished, for example, by increasing the numbers of antibodies produced upon immunization with the antigen (e.g., a quantitative improvement), or by altering the profile of the immune response, such as from a Th1 response to a Th2 response (e.g., a qualitative improvement).

The invention also pertains to methods for eliciting or increasing a host's humoral and/or cell-mediated immune response, comprising administering to a vertebrate host an effective amount of an immunogenic composition comprising an antigen and an adjuvant containing 0.01–70% v/v of glycerides selected from the group consisting of monoglycerides, diglycerides, and mixtures thereof, said glycerides having the formulas (I) to (V) as described above. In a particular embodiment, the immune response is elicited by mucosal administration of the composition.

The invention also pertains to methods for eliciting or increasing a vaccinate's humoral and/or cell-mediated immunity, for a protective immune response, comprising administering to a vertebrate host an effective amount of a vaccine composition comprising an antigen and an adjuvant containing 0.01–70% v/v of glycerides selected from the group consisting of monoglycerides, diglycerides, and mixtures thereof, said glycerides having the formulas (I) to (V) as described above. In a particular embodiment, the immune response is elicited by mucosal administration of the composition.

DETAILED DESCRIPTION OF THE INVENTION

The immune system uses many mechanisms for attacking pathogens; however, not all of these mechanisms are necessarily activated after immunization. Protective immunity induced by vaccination is dependent on the capacity of the vaccine to elicit the appropriate immune response to resist or eliminate the pathogen. Depending on the pathogen, this may require a cell-mediated and/or humoral immune response. It is often desirable to enhance the immunogenic potency of an antigen in order to obtain a stronger immune response in the organism being immunized and to strengthen host resistance to the antigen-bearing agent. Generally, a substance that enhances the immunogenicity of an antigen with which it is administered (either simultaneously or close in time) is known as an adjuvant. As used herein, the term "adjuvant" in relation to the compositions of the invention is intended to encompass compositions having a traditional adjuvant effect (e.g., enhancing the immunogenicity of an antigen by increasing or altering the antibody response thereto), as well as compositions which enhance the presentation of the antigen to the appropriate tissue or cells (e.g., an antigen delivery vehicle).

For intranasal administration, an antigen must be applied to the mucosa in such a manner that it is able to penetrate or be absorbed through the mucosa or the lymphoid tissue to the immunocompetent cells, and such that it is not washed away by the nasal secretions. The antigen should also be administered onto the nasal mucosa in such a way that the antigen-presenting cells absorb the antigen and transport it to the local lymphoid system. In order to penetrate the mucus, the delivery vehicle must have a certain degree of biocompatibility with the mucus membrane and hence have a certain degree of hydrophilicity and hydrophobicity.

Work described herein relates to the utility of compositions described herein as mucosal adjuvants. Accordingly, this invention pertains to compositions, e.g., immunogenic or vaccine compositions, comprising an antigen and an adjuvant containing 0.01–70% v/v of glycerides selected from the group consisting of monoglycerides, diglycerides, and mixtures thereof. For example, the monoglycerides and/or diglycerides may be substituted. Monoglycerides and diglycerides that are incorporated into the compositions of this invention are represented by the general formula (I):

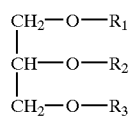

wherein $R_1$, $R_2$, and $R_3$ are independently selected from the group consisting of saturated or unsaturated $C_{6-24}$ fatty acids, water soluble polymers, and mixtures thereof; provided that the glyceride contains at least one water soluble polymer. The adjuvant can also contain small amounts of substituted or unsubstituted triglycerides.

Any saturated or unsaturated $C_{6-24}$ fatty acid can be selected, including, but not limited to, fatty acid residues derived from caproic acid, capric acid, caprylic acid, arachidonic acid, propionic acid, lauric acid, myristic acid, palmitic acid, oleic acid, linoleic acid and linolenic acid. The fatty acid residues may be a single residue or a mixture of two or more residues. They can be derived from natural or synthetic sources, such as fats and oils. Commercially available glycerides can be used or they can be synthesized enzymatically by means of lipases, including both specific and non-specific lipases, which place the fatty acids on specific places such as 1; 2; 1,2; 1,3; and specific racemic structures as well, etc. For example, glycerol (0.92 g) adsorbed onto 1 g silica gel is suspended with 20 ml tBuOMe. Vinyl caprylate (3.4 g) and lipase (50 mg) from *Rhizopus delemar* were added to the suspension. The mixture was stirred at room temperature for 96 hours and the reaction progress was monitored by means of TLC. After removal of the solid components by filtration and evaporation of the solvent, a crude reaction mixture was obtained which contained about 91% of 1,3 dicaprylin glyceride.

The water soluble polymer can be one which renders the glyceride more hydrophilic (preferably fully soluble without the use of surfactant) in aqueous solutions, particularly physiologically acceptable vehicles for vaccine administration. A desirable water soluble polymer is one that is biocompatible with the tissue to which it is administered, particularly the mucus membranes. Suitable water soluble polymers having these properties, include but are not limited to, polyethyleneglycol, polyethyleneglycol derivatives (including, but not limited to, amino-PEG, nucleophilic-PEG, PEG-thiol, PEG-succinate, PEG-succinimide, PEG-tresylate, carboxymethylated-PEG, PEG-propionic acid, PEG-silanes, PEG-phospholipids, biotin-PEG and PEG-orthopyridyl-disulfide), glycofurol, propyleneglycol, dextrans and saccharides.

Preferred are polyethylene glycol polymers having from about 2 to about 30 polyethyleneglycol units ($PEG_{2-30}$), with from about 3 to about 6 polyethyleneglycol units ($PEG_{3-6}$) being most preferable. One or two PEG moieties, other water soluble polymers or combinations can be incorporated into the glyceride formula. The water soluble moiety can reside at any one of the $R_1$, $R_2$, or $R_3$ positions of the glyceride.

The polymers can be attached to the glyceride via covalent bonds formed chemically or enzymatically. The polymers may be acylated to the glyceride or linked using ester bonds such as, for example, by esterase-mediated synthesis. For example, solketal can be mixed with polymerchloride in triethanolamine and trichloromethane, whereafter the free glycerol bonds are deprotected by heating in dilute aqueous acetic acid. With excess of caproyl chloride in the presence of triethylamine and 4-dimethylaminopyridine as catalyst, the fatty acids are linked to the free glycerol bonds. The results of this synthesis will be a caproyl/polymer glyceride.

In one embodiment of the invention, one or two of the groups $R_1$, $R_2$, and $R_3$ are replaced by bound antigen. The antigen can be bound to the glyceride moiety by covalent attachment. In another embodiment of the invention, the composition comprises a mixture of monoglycerides and diglycerides such that the v/v-% ratio of monoglycerides to diglycerides is in the range of 0.1:99.9 to 99.9:0.1, and preferably in the range of 5:95 to 95:5. In a further embodiment of the invention, the water soluble polymer is a $PEG_{3-6}$ residue of polyoxyethylene having 3 to 6 polyoxyethylene units. The invention further relates to the described compositions wherein the glycerides have a structure selected from the group consisting of:

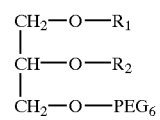

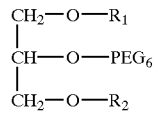

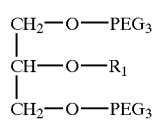

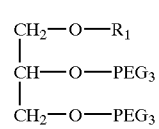

wherein $R_1$, and $R_2$, are defined above.

In one embodiment of the invention, $R_1$, $R_2$, and $R_3$ are selected from saturated $C_{6-14}$ fatty acids, more preferably saturated $C_{8-10}$ fatty acids. In another embodiment of the invention, the glycerides have a concentration from about 0.1% to about 99%, preferably from about 0.5 to about 20%, and more preferably from about 1 to about 15% by weight. In particular embodiments of the invention, chiral carbons in the glyceride are either S- or R-form.

The adjuvant compositions of the invention modulate the immune response to one or more antigens; that is, the immunogenic or vaccine composition is capable of eliciting a vaccinated host's cell-mediated immunity to generate an immune response, e.g., a protective immune response, to at least one pathogenic antigen.

The antigen of this invention can be combined with one or more of the adjuvant compositions according to the invention, and this formulation can be used to elicit an immune response to the antigen in a vertebrate such as a mammalian host. For example, the antigen can be selected from the group including, but not limited to, tetanus toxin, influenza virus, diphtheria toxoid, HIV gp120, IgA-protease, insulin peptide B, vibriose, salmonella, *Spongospora subterranea*, respiratory syncytial virus (RSV) (e.g., an RSV subunit vaccine), *Haemophilus influenza* outer membrane proteins, *Helicobacter pylori* urease and recombinant pilins of *Neisseria meningitidis* and *N. gonorrhoeae*, or a portion thereof which retains the ability to stimulate an immune response. The ability of portions of a given antigen to stimulate an immune response can be assessed by art-recognized methods, such as enzyme immunoassay against specific peptides within a portion to detect antibodies that recognize that particular portion (humoral response) or a delayed-type hypersensitivity assay against specific peptides in that portion to detect a cell-mediated immune response thereto.

The term "antigen" is intended to include a molecule which contains one or more epitopes which stimulate a host's immune system to produce a humoral, cellular and/or secretory immunological response. The antigen of the invention can be a subunit antigen, as well as killed, attenuated or inactivated bacteria, viruses, protozoa, fungi, parasites or other microbes. The antigen can be, for example, a protein, peptide, polysaccharide, lipid or DNA antigen. Suitable antigens can be derived from, for example, Pasteurella, Actinobacillus, Chlamydia, Moraxella, Neisseria, Streptococcus, Haemophilus, Salmonella and Eimeria species, as well as rotaviruses, herpes viruses (e.g., BHV-1, EHV-1), PRV, parvovirus, rabiesvirus, influenza viruses, parainfluenza viruses, hepatitis viruses, HIV, picornaviruses, tumor antigens, hormones, hormone analogs and the like.

The antigen in the formulation according to the invention is suitable for inducing vaccination, immunization, treatment of allergy, treatment of cancer, treatment of infectious disease, treatment of an autoimmune disease or the treatment of a disease which is affected by the immune system. The antigen may, therefore, be a vaccine such as anti-bacterial, anti-viral, anti-fungal, anti-prion, anti-parasitic vaccine or components produced by micro-organisms such as IgA-proteases, Protein p38, Protein p43 or mucinase. The antigen may also be an allergen such as house dust mite, domestic cat allergen, rye grass pollen, short ragweed pollen, midge, egg white, milk protein, bee venom, white faced hornet allergen etc. or components responsible for inducing autoimmune diseases such as myelin, insulin peptide B and the like. The antigen can also be used as a vaccine for the treatment of infectious diseases, such as herpes, HIV, pappiloma, candida, multiple sclerosis, treatment of autoimmune diseases such as diabetes, hypo- and hyperthyroidism, psoriasis, arthritis or the treatment of cancer.

Suitable antigens for the vaccine compositions of the present invention include any entity capable of producing antibody or cell-mediated immunological response directed specifically against that entity in a vertebrate exposed to the antigen. One or more antigens may be employed, The antigen or antigens may be derived from pathogenic microorganisms including viruses, bacteria, mycoplasmas, fungi, protozoa and other parasites. Further, the antigen or antigens may be derived from sources other than microorganism, for example, cancer cells or allergens. The antigen or antigens may be all or part of a pathogenic microorganism, or all or part of a protein, glycoprotein, glycolipid, polysaccharide or lipopolysaccharide which is associated with the organism.

Pathogenic microorganism from which antigens may be derived or produced for vaccine purposes are well known in the field of infectious diseases, as listed in, for example, Medical Microbiology, Second Edition, (1990) J. C. Sherris (ed.), Elsevier Science Publishing Co., Inc., New York.

The antigen may be used in a particulate form or dissolved. The formulation is especially suitable for dissolved antigens, however, particulate forms are also easy to prepare into the formulation. For vaccination and immunization, the particulate form has often been advantageous but for inducing tolerance, e.g., for the treatment of allergy or autoimmune diseases, a dissolved antigen is preferred.

The immunological adjuvant activity of an adjuvant according to the invention, either alone or with a particular antigen, can be assessed using methods known in the art, such as ELISAs, hemagglutination assays and neutralization assays. As used herein, "immunological adjuvant activity" is intended to mean the ability to potentiate an immunological response in a host to which the adjuvant and antigen are administered. Typically the adjuvant will be administered with the antigen, either in the same admixture or composition (see, for example, International Publication No. WO 93/05789), or at the same time but in a separate composition or formulation. The antigen can be bound to the adjuvant (e.g., covalently) or merely admixed therewith. The adjuvant can also be administered prior to or subsequent to the administration of the antigen. Adjuvant activity includes, but is not limited to, the ability to enhance the immunological response to the antigen by increasing the immunogenicity of the antigen or by reducing the dose or level of antigen required to produce an immune response.

As used herein, an "immune response" or "immunological response" to a particular antigen is intended to include the production of a secretory, cellular, humoral or antibody-mediated response to the antigen (or a generalized response). The manifestation of the response in the immunized host can include the production of antibodies (e.g., IgA, IgD, IgE, IgG or IgM antibodies), proliferation of B and/or T lymphocytes, stimulation of cytotoxic T lymphocytes that recognize antigen-presenting cells, expansion of T cell populations and the potentiation of signals which cause differentiation, activation or growth of cells of the immune system.

Typically the administration of the adjuvants of the invention will cause or result in an enhanced immune response to an antigen of interest. In this context, "enhanced" is intended to mean that the immune response to the antigen is quantitatively greater and/or qualitatively better in the presence of the adjuvant than in the absence of the adjuvant. Comparisons of immune responses in the presence and absence of the adjuvants can be performed by routine methods, such as antibody titer comparisons by radioimmunoassay or ELISA of formulations comprising adjuvant and antigen, and appropriate controls. The enhanced immune response can be a result of a direct effect on the immune system of the individual (e.g., a priming of T and B cells to increase the response to the antigen) or can result from a more advantageous presentation of the antigen to the mucus membrane (e.g., by providing better adhesion to the mucus membrane to allow a longer period of contact between the antigen and the mucus membrane, or by enhancing the absorption of the antigen across the mucus membrane, for example by increasing the permeability of the mucus membrane).

Adjuvants of the invention can be used as described herein as adjuvants to enhance the immunological response to an antigen. In a particular embodiment the adjuvant is a mucosal adjuvant. For example, the adjuvant can be used in a composition to immunize a mammal against a particular pathogen or subunit antigen, or to prime an immune response to a particular antigen.

The method of the present invention comprises administering to a mammal, particularly a human or other primate, an immunologically effective dose of an immunogenic or vaccine composition comprising an antigen and an adjuvant amount of an adjuvant of the invention. As used herein, an "adjuvant amount" or an "effective amount" of the adjuvant is intended to mean an amount which enhances an immune response to a coadministered antigen. For example, doses of from about 0.01% to about 40%, and more particularly from about 0.1% to about 20% will typically be effective to provide an adjuvant effect; however, variations in these dosage ranges will occur depending upon the particular adjuvant. Moreover, the particular dosage will depend upon the age, weight and medical condition of the mammal to be treated, as well as on the method of administration. Suitable doses will be readily determined by the skilled artisan.

The vaccine or immunogenic composition can be optionally administered in a pharmaceutically or physiologically acceptable vehicle, such as physiological or phosphate buffered saline, water, dextrose, ethanol polyols (such as glycerol or propylene glycol), and combinations thereof. The formulation according to the invention can be a suspension, an emulsion or a dispersion and can provide the adjuvant in admixture with a dispersing or wetting agent, suspending agent, and/or one or more preservatives. Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate etc. Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591), methylcellulose; alginates such as, e.g., sodium alginate, etc. Suitable examples of preservatives for use in formulations according to the invention are parabens, such as methyl or propyl p-hydroxybenzoate, and benzalkonium chloride.

For application to the rectal or vaginal mucosa, suitable formulations for use according to the invention include suppositories (emulsion or suspension type), enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives, e.g., enhancers or surfactants, can also be incorporated.

For application to the nasal mucosa, nasal sprays and aerosols for inhalation are suitable compositions for use according to the invention. In a typical nasal formulation, the active substance is present in the form of a particulate formulation optionally dispersed in a suitable vehicle. The pharmaceutically acceptable vehicles and excipients and optional other pharmaceutically acceptable materials present in the composition such as diluents, enhancers, flavouring agents, preservatives and the like are all selected in accordance with conventional pharmaceutical practice in a manner understood by the persons skilled in the art. After administration of a nasal formulation according to the invention, the antigen may be adsorbed onto the nasal mucosa. The adsorption to the mucosa is believed to lead to a less irritating effect than when, e.g., a liquid vehicle such as one containing a penetration enhancer or promoter is employed. Other mucosal surfaces which are suitable for the administration of formulations of the invention are the nose, lungs, mouth, eye, ear, gastrointestinal tract, genital tract, vagina, rectum or skin, or in fish to the gills. Such formulations may also be suitable for application to seeds or leaves of plants.

For application to the skin, the formulations according to the invention may contain conventional non-toxic pharmaceutically acceptable carriers and excipients including micro-spheres and liposomes. The formulations include creams, ointments, lotions, liniments, gels, hydrogels, solutions, suspensions, sticks, sprays, pastes, plasters, and other kind of transdermal drug delivery systems. In one embodiment, the formulation can be administered as nasal spray, nasal drops, nasal powder, nasal foam or as nasal ointment to the mucosal surface or the adenoids of the nose or as oral spray, oral drops, oral powder, oral foam or as oral ointment especially directed to the buccal area or to the tonsils of the mouth. The formulation can also be in the form of eye drops.

Pharmaceutically acceptable excipients may include emulsifying agents, antioxidants, buffering agents, preservatives, humectants, penetration enhancers, chelating agents, gelforming agents, ointment bases, perfumes, and skin protective agents. Examples of emulsifying agents are naturally occurring gums, e.g. gum acacia or gum tragacanth, naturally occurring phosphatides, e.g. soybean lecithin, and sorbitan monooleate derivatives. Examples of antioxidants are burylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and Azone®. Examples of chelating agents are sodium EDTA citric acid, and phosporic acid. Examples of other excipients are edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil; and of polymers such as carmelose, sodium carmelose, hydroxypropylmethylcellulose, hydroxyethylcellulose, hydroxypropylcellulose, chitosane, pectin, xanthan gum, carragenan, locust bean gum, acacia gum, gelatin, and alginates. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween®). The formulations mentioned above for topical administration may also be applied to the skin, the gills of fish or to the outer surface or seeds of plants. Formulations of the invention may also be suitable for direct application or for introduction into relevant orifice(s) of the body, e.g. the rectal, urethral, vaginal or oral orifices. The formulation may simply be applied directly on the part to be immunized such as, e.g., the mucosa.

Many mucosal formulations need some specialized mixture of excipients. Therefore many formulations may comprise one or more surfactants and/or absorption promoters and/or water absorbing polymers and/or substances which inhibit enzymatic degradation and/or alcohols, organic solvents, oils, pH-controlling agents, solubilizers, stabilisers, HLB-controlling agents, viscosity controlling agents, preservatives, ormotic pressure controlling agents, propellants, air displacement, water and mixture thereof. The surfactants may be selected from nonoxynol, octoxynol, tweens, spans sodium lauryl sulfate, sorbitan monopalmitate; absorbing promoters may be selected from polyoxyethylene alcohol ethers, bile salts and derivatives thereof, fusidic acid and derivatives thereof, oleic acid, lecitin, lysolechitins, Tween® 20–85, mono-/di- and triglycerides, shitosan, cyclodextriner, water absorbing polymers may be selected from glycofurols and derivatives thereof, polyethyleneglycol 200–7500 and derivatives thereof, polyvinylpyrrolidone, polyacrylic acid, propyleneglycol, gelatine, cellulose and derivatives thereof, substances which inhibit enzymatic degradation may be selected from aprotinin, DFP, carbopol; oils may be selected from vegetable oil, soybean oil, peanut oil, coconut oil, maize oil, olive oil, sunflower oil, Miglyols; pH-controlling agents may be selected from acetic acid, hydrochloric acid, nitric acid, potassium metaphosphate, potassium phosphate, sodium acetate, ammonia, sodium carbonate, sodium hydroxide, sodium borate, trolamine; solubilizers may be selected from alcohol, isoporpyl alcohol, water glycofurol, polyethyleneglycole 200–7500; stabilisers such as cyclodextrines; HLB controlling agents may be selected from Tween® 20–85, Span 20–80, Brij 30–98, acacia; viscosity controlling agents may be selected from cellulose and derivatives thereof, Tweens® and derivatives thereof, polyethyleneglycole and derivatives thereof, cetyl alcohol, glycerine, porpylene glycol, sorbitol, gelating; preservatives may be selected from benzalkonium salt, benzyl alcohol, phenol, thimerosal, pnenylmercuric nitrate, phenylethyl alcohol, chlorobutanol, cetypyridinium chloride; osmotic pressure controlling agents may be selected from dextrose, sodium chloride, mannitol; and propellants may be selected from dichlorodifluoromethane, dichlorotetrafluoroethane, trichloromonofluoromethane and other non-ozone damaging propellants such as butane; air displacement may be nitrogen.

For liquid compositions it is essential that the effective amount of the antigen can be administered in an appropriate volume. For nasal administration the volume should not exceed about 300 µl for a human subjects. A larger volume can be disagreeable to the patient and will drain out anteriorly through the nostrils or posteriorly toward the pharynx. The result is that a part of the antigen and/or the vaccine is lost from the absorption site. The volume is preferably from about 20 µl to about 125 µl and preferably administered into one nostril. For the administration to the buccal and rectal area, a volume not exceeding 10 ml should be used. For the administration to the eye and the ear a volume not exceeding 300 µl should be used. For the administration to the lungs, a volume not exceeding 2 ml should be used. For the administration to the vagina, a volume not exceeding 30 ml should be used. For administration to the gastrointestinal tract a volume not exceeding 100 ml should be used.

The vaccine composition may optionally comprise additional components, such as buffering agents, preservatives, emulsifying agents and adjuvants, such as vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'-N'bis (2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions; lipopolysaccharides such as MPL® (3-O-deacylated monophosphoryl lipid A (RIBI ImmunoChem Research, Inc., Hamilton, Mont.); mineral gels, and immunostimulating oligonucleotides. The antigens of this invention can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed.

Antigens of the present invention can also be administered in combination with bacterial toxins and their attenuated derivatives as additional adjuvants or carrier molecules. Other suitable carrier molecules include serum albumins, keyhole limpet hemocyanin, immunoglobulin molecules, immunoglobulin, ovalbumin, polysaccharides (e.g., sepharose, agarose, cellulose), inactive virus particles, and amino acid copolymers. The antigens of the invention can also be administered in combination with lymphokines including, but not limited to, interleukin-2, IFN-γ and GM-CSF. The antigens of the invention can also be expressed in vivo after administration of DNA encoding these antigens.

The vaccines can be administered to a human or animal by a variety of routes, including but not limited to parenteral, intraarterial, intradermal, transdermal (such as by the use of slow release polymers), intramuscular, intraperitoneal, intraoccular, sublingual, intravenous, subcutaneous, oral and intranasal routes of administration. In a preferred embodiment, the composition is administered through a mucus membrane. The amount of antigen employed in such vaccines will vary depending upon the identity of the antigen. Adjustment and manipulation of established dosage ranges used with traditional carrier antigens for adaptation to the present vaccine is well within the ability of those skilled in the art. The vaccines of the present invention are intended for use in the treatment of both immature and adult warm-blooded animals, and, in particular, humans. Administration of the immunogenic or vaccine compositions of the invention can also be accomplished using gene therapy methods (see, e.g., U.S. Pat. No. 5,580,859 and published PCT application publication nos. WO 93/19183 to Robinson et al. and WO 97/44446 to Malone et al.).

The mucosal adjuvant action of adjuvants of the invention has a number of important implications. The mucosal adjuvanticity can increase the concentration of protective antibodies produced against a mucosally-administered antigen in the vaccinated organism. As a result, effective vaccination can be achieved with a smaller quantity of antigen than would be normally required. This reduction in the required amount of antigen may lead to more widespread use of vaccines which are difficult and costly to prepare. Additionally, the use of adjuvants of the invention can enhance the ability of antigens which are weakly antigenic or poorly immunogenic, particularly when administered mucosally, to elicit an immune response. It may also provide for safer vaccination when the antigen is toxic at the concentration normally required for effective mucosal immunization. By reducing the amount of antigen, the risk of toxic reaction is reduced. It may also provide for safer vaccination by enabling the use of an antigen or vaccine formulation which is safe by mucosal route but toxic by parenteral route.

Typically, vaccination regimens call for the administration of antigen over a period of weeks or months in order to stimulate a "protective" immune response. A protective immune response is an immune response sufficient to prevent infection or reduce the severity of infection (compared with severity of infection in the absence of the elicited immune response) caused by a particular pathogen or pathogens to which the vaccine is directed. The use of adjuvants of the invention may reduce the time course of effective vaccination regimens. In some instances, it may result in the generation of a protective response in a single dose. The vaccine compositions of this invention are also useful therapeutically, to reduce the number and severity of symptomatic episodes in subjects already infected with the antigen. The vaccine compositions may also be used as an oral booster immunization for parenterally administered antigens.

The formulation according to the invention is especially suitable for humans, including toddlers, adolescents, teenagers, adults and elderly. The nature of the formulation provides the ability to enhance the immune response to a variety of pathogens, and therefore the formulation may be used for subjects with various conditions such as humans with disease, e.g., splenectomized subjects, subjects with cancer, subjects using anticancer drugs, subjects using anti-asthmatic drugs, subjects using antiinflammatory drugs, subjects with hyper-and hypothyroidea.

The formulation according to the invention is also suitable for administration to animals such as horses, sheep, dogs, cats, cows, pigs, goats, rabbits, wild animals and laboratory animals such as mice, rats, guinea pigs, hamsters, rabbits, dogs, cats or monkeys; to birds such as chickens, turkeys, ducks, ostrich, tropical birds or wild birds; or to fish such as farm fish, e.g., salmon or aquarium fish. For animals, the concentration of each component may need to be adjusted. For example for sheep, the nasal cavity has extremely high humidity, which may require addition of water absorbing excipients to the formulation, and for fish, the formulation may need to be microencapsulated or in such a form that the formulation will be absorbed to the gills.

The adjuvant compositions of the invention can also be used to enhance the bioactivity (e.g., immunogenicity) and/or uptake of bioactive agents (e.g., antigens) in plants. Bioactive agents which can be used in conjunction with the adjuvant compositions of the invention can be, e.g., herbicides, insecticides, fungicides, plant growth regulators, fertilizers and vaccines. Many appropriate bioactive agents are commercially available and can generally be applied at rates recommended by the supplier. The particular amount of bioactive ingredient for use in formulations of the invention will vary with the specific plant or plant growth medium with which it is to be contacted, the general location of an application, i.e., sheltered areas such as greenhouses as compared with exposed areas such as fields, and the type of formulation (e.g., aerosol, liquid, solid). The formulation can be used on any type of plant, including, but not limited to, grasses (e.g., blackgrass, cheat grass, crabgrass, barnyard grass, goosegrass, ryegrass, Italian grass), crop plants (e.g., wheat, oats, sorghum, corn, sugarbeets, canola, soybean, cotton, tobacco, potato, fruit trees, cucumber, tomato, banana, beans, peppers, melons) and ornamental plants (shrubs, trees, flowers). The formulation can be applied to the leaves, seeds, fruits, bark or wood, or can be admixed with the growth medium (e.g., peat or soil). The formulation can be applied to plants individually (e.g., with a spray applicator) or en masse (e.g., from an aircraft). The delivery of antigens to a plant using the adjuvant compositions of the invention can be used to immunize plants against pathogens (e.g., by the generation of plantibodies or by the activation of local and systemic acquired resistance (see, for example, Agrios, Plant Pathology, fourth edition (Academic Press, 1997), pages 108–114, and references cited therein).

The following Examples are offered for the purpose of illustrating the present invention and are not to be construed to limit the scope of this invention. The contents of all references, patents and published patent applications cited throughout this application are hereby incorporated by reference.

EXAMPLES

Example I

Tetanus Toxoid

Mice (BALB/c) are intranasally administered a 5 µl formulation containing 1.5 µl tetanus toxoid vaccine (Lyfjathroun, Reykjavik, Iceland) in the following formulations: (I) isotonic saline; (II) 20% $PEG_6$-CCG (Softigen®; Hüls AG, Witten, Germany) which is a monoglyceride/diglyceride mixture of caprylic and capric acid containing 6 polyoxyethylene ($PEG_6$) units in isotonic saline; and (III) 20% mixture of monoglyceride/diglyceride mixture of caprylic and capric acid (Imwitor®) solubilized with Tween® 20 (22:78) in isotonic saline (CCG-polysorbate 20 (CCG-PS); WO 94/17827). Four weeks after the first vaccination, the mice received a booster containing the same vaccines. One week later, blood samples were drawn, and the following serum IgG responses were obtained:

TABLE 1

| Formulation | Serum IgG response |
| --- | --- |
| I | 0.01 |
| II | 2.1 |
| III | 0.65 |

These results show that the non-toxic PEG6-CCG (formulation II) produces a significantly enhanced IgG response compared to a vaccine formulation as described in WO 94/17827 (formulation III).

Example II

Influenza Virus

Twenty Balb/c mice were immunized with influenza virus vaccine (HA molecules from strain Harbin). The influenza HA molecules were formulated with 0%, 1%, 5% and 20% PEG6-CCG according to the invention. Four weeks post primary immunization the mice received a booster containing the same formulations. One week post booster administration, the following results were achieved:

| % Adjuvant | Conc. IgG (Serum) |
| --- | --- |
| 0% | 1.1 |
| 1% | 4.2 |
| 5% | 6.8 |
| 20% | 8.4 |

Example III

Mice (BALB/c) are intranasally administered a 5 µformulation containing 20% $PEG_6$-CCG, which is a monoglyceride/diglyceride mixture of caprylic and capric acid containing 6 polyoxyethylene ($PEG_6$) units, in isotonic saline, with the addition of the following antigens: (1) 1 µg HA influenza virus vaccine per mouse; (II) 1.5 Lf (limit of flocculation) tetanus toxoid vaccine; (III) 1.5 Lf diphtheria toxoid vaccine; (IV) 1 µg rgp 120 HIV vaccine; (V) 1 µg IgA-protease as vaccine and (VI) 1 µg insulin peptide B. Four weeks after the first vaccination, the mice received a booster containing the same vaccines. One week later, blood samples were drawn and analyzed.

Example IV

Tetanus toxoid and Diphtheria Toxoid

Human volunteers are intranasally administered a 100 µl formulation containing 12 Lf tetanus toxoid and 12 Lf diphtheria toxoid vaccine in following formulations: (I) isotonic saline; (II) $PEG_6$-CCG, which is a monoglyceride/ diglyceride mixture of caprylic and capric acid containing 6 polyoxyethylene ($PEG_6$) units, in isotonic saline; (III) 5% $PEG_6$-CCG in isotonic saline; and (IV) 1% $PEG_6$-CCG in isotonic saline. Four weeks after the first vaccination, the participants received a booster containing the same vaccines. During the study each volunteer is sampled (blood and saliva sample) weekly for IgG and IgA analysis.

Example V

Mice (BALB/c) are given 1.5 Lf tetanus toxoid vaccine in 20% $PEG_6$-CCG, which is a monoglyceride/diglyceride of caprylic and capric acid containing 6 polyoxyethylene ($PEG_6$) units, in isotonic saline. The formulation is administered (I) 5 µl intranasally; (II) 5 µl orally into the mucosa of the mouth; (III) 5 µl vaginally; (IV) 5 µl rectally; and (V) 5 µl dermally. Four weeks after the first vaccination, the mice received a booster containing the same vaccines. One week later, blood samples were drawn.

Fifteen Balb/c mice were immunized with influenza virus vaccine (HA molecules from strain Nanchang). The influenza HA molecules were formulated with 5% PEG6-CCG according to the invention and administered intranasally, buccally and rectally. Four weeks post primary immunization the mice received a booster containing the same formulations by the same route. One week post booster administration, the following results were achieved:

| Route | Adsorbance (OD 492 nm) |
|---|---|
| Nasal | 0.300 |
| Buccal | 0.334 |
| Rectal | 0.155 |

Example VI

A formulation containing 10% $PEG_6$-CCG, which is a monoglyceride/diglyceride of caprylic and capric acid containing 6 polyoxyethylene ($PEG_6$) units, in isotonic saline and a selected vaccine composition is administered as follows: (I) 1.5 Lf tetanus toxoid to mice; (II) 6 Lf tetanus toxoid to rabbits; (III) 20 Lf tetanus toxoid to sheep; (IV) 12 Lf tetanus toxoid to human volunteers; (V) 3 µg vibriose vaccine to salmon; (VI) 3 µg salmonella vaccine to chicken; and (VII) 3 µg *Spongospora subterranea* antigen to potato plants. Four weeks after the first vaccination, a booster containing the same vaccines was administered. One week later, blood samples were withdrawn (except for the plant in (VII)). For the plant in (VII) the potato plant was challenged with the fungi one month after booster administration.

Example VII

Mice (BALB/c) are intranasally administered 5 µl formulation, containing (I) tetanus toxoid or (II) pneumococcus, coupled to monoglycerides and diglycerides of caprylic and capric acid. This pro-vaccine is administered in 20% concentration. Four weeks after the first vaccination, the mice received a booster containing the same vaccines. One week later, blood samples were drawn.

To evaluate the effects of $PEG_6$-CCG on vaccine antigens following intranasal administration, experiments were carried out using a number of viral and bacterial antigens, including influenza vaccine, respiratory syncytial virus (RSV) subunit vaccine, non-typeable *Hemophilus influenza* outer membrane proteins (OMPs), *Helicobacter pylori* urease, recombinant pilins of *Neisseria meningitidis* and *N. gonorrhoeae*. The results of this analysis are set forth in the following examples.

Example VIII

Influenza vaccines

This example summarizes the evaluation of the adjuvant effects of CCG-PS and PEG-CCG on the immune response to A/Udorn vaccine (a monopool split Influenza vaccine; Wyeth Lederle Vaccines and Pediatrics, West Henrietta, N.Y.) and the contribution of the local immune response to protection of the respiratory tract from descending disease.

TABLE 2

| Group | Immunogen | Dose/Route/Volume |
|---|---|---|
| A | A/Udorn/307072(H3N2) | $1.8 \times 10^5$ $TCID_{50}$/IN/5 µl |
| B | none | None |
| C | A/Udorn vaccine | 1.0 µg HA/IM/50 µl |
| D | A/Udorn vaccine | 1.0 µg HA/IN/5 µl |
| E | A/Udorn vaccine in 10% CCG-PS | 1.0 µg HA/IN/5 µl |
| F | A/Udorn vaccine in 5% $PEG_6$-CCG | 1.0 µg HA/IN/5 µl |

BALB/c mice 8 per group
Vax: days 0, 19 and 38
Challenge: day 70
Virus titration: day 74
HA = hemagglutinin Serological data both from ELISA and hemagglutination inhibition (HI) assays indicated that the $PEG_6$-CCG formulation induced higher serum IgGI and HI titers than did the CCG-PS formulation. The intranasally-introduced $PEG_6$-CCG formulation generated systemic antibody response comparable to that elicited by parenterally administered standard vaccine.

ELISPOT data confirm that ability of $PEG_6$-CCG, like the first generation CCG-PS formulation, to heighten the local immune response to influenza vaccine, as demonstrated by the increased number of IgA-secreting B cells found in the nasal lymphoid tissues compared to that elicited by intranasal administration of vaccine alone. Vaccine administered via the intramuscular route did not result in a local response above the background found in naive mice.

TABLE 3

The $PEG_6$-CCG formulation facilitates humoral antibody responses to nasal administered influenza vaccine.

| Immunogen/Route | HI GMT | IgG1 GMT | IgG2a GMT | IgA secreting cells/$10^6$ nasal lymphoid cells |
|---|---|---|---|---|
| A/Udorn/IN | 512 | 19,426 | 436,556 | 463 |
| none | 8 | 13 | 13 | 1 |
| A/Udorn vax/IM | 215 | 48,537 | 1,254 | 6 |
| A/Udorn vax/IN | 25 | 732 | 73 | 22 |
| A/Udorn vax/CCG-PS/IN | 181 | 20,556 | 228 | 150 |
| A/Udorn vax/$PEG_6$-CCG/IN | 512 | 88,533 | 173 | 73 |

As shown in the table below, mice previously exposed to infectious virus are completely protected from subsequent challenge with the homologous virus. Virus was not recoverable from pulmonary or nasal tissue. In contrast, naive mice are readily infected with the A/Udorn virus, both in the lung and nasal tissues. Virus was also recovered from the nasal tissue of all mice which received parenteral or non-adjuvanted intranasal vaccine. These data suggest that the immune responses elicited with CCG-PS or PEG$_6$-CCG adjuvanted vaccine protect the upper respiratory tract from virus challenge. Virus recovery from the nasal tissue was significantly reduced in those animals receiving intranasal vaccine adjuvanted with either CCG-PS or PEG$_6$-CCG. Some protection of the lower respiratory tract is evident independent of vaccine formulation or route of delivery.

TABLE 4

Immune responses elicited by CCG-PS or PEG$_6$-CCG adjuvanted intranasal influenza vaccine protect the respiratory tract from virus challenge.

| Immunogen/Route | % positive nose | % positive lung | Virus recovery from nose GMT | Virus recovery from lung GMT |
|---|---|---|---|---|
| A/Udorn/IN | 0 | 0 | 200 | 200 |
| none | 100 | 75 | 53,724 | 40,788 |
| A/Udorn vax/IM | 190 | 0 | 30,211 | 200 |
| A/Udorn vax/IN | 100 | 25 | 6,324 | 563 |
| A/Udorn vax/CCG-PS/IN | 75 | 0 | 2,081 | 200 |
| A/Udorn vax PEG$_6$-CCG/IN | 25 | 25 | 621 | 1002 |

200 TCID$_{50}$ = <400 (assay limit of detection), all negative samples were assigned a value of 200

Example IX

RSV F Protein

This example summarizes the evaluation of the adjuvant effects of CCG-PS and PEG$_6$-CCG on the immune response to RSV F protein, and the contribution of the local immune response to protection of the respiratory tract from descending disease.

TABLE 5

| Group | Immunogen | Dose/Route/Volume | Vax schedule |
|---|---|---|---|
| A | F protein | 3 µg/IN/5 µl | Days 0, 7 14 |
| B | F protein in 20% CCG-PS | 3 µg/IN/5 µl | Days 0, 7 14 |
| C | F protein in 5% PEG$_6$-CCG | 3 µg/IN/5 µl | Days 0, 7 14 |

TABLE 5-continued

| Group | Immunogen | Dose/Route/Volume | Vax schedule |
|---|---|---|---|
| D | F protein on Alum | 3 µg/IM/100 µl | Day 0 |
| E | RSV A2 | 2 × 10$^6$ pfu/IN/50 µl | Day 0 |

BALB/c mice, 10 per group

Fprotein-specific serum antibody responses—Intranasal vaccination with F protein/PBS elicited a circulating IgG anti-F response with a titer of approximately 26,000. However, by combining F protein with either CCG-PS or PEG$_6$-CCG, statistically elevated titers (p<0.05) of total IgG, IgG1 and IgG2a were obtained (see Table 6). In addition, a significant serum IgA titer was only elicited by the vaccine formulated with PEG$_6$-CCG. This observation has been made consistently and may be the result of different immunological properties of PEG$_6$-CCG.

Fprotein-specific mucosal Ig responses—IgA was observed in the nasal and vaginal washes of mice vaccinated with F/PEG$_6$-CCG, which reflects the stimulation of serum IgA by this vaccine combination (see Table 6). In this experiment, the level of IgA in the nasal washes was found to be higher than that present in mice recovering from infection with live RSV.

TABLE 6

The immune response of BALB/c mice vaccinated intranasally with combinations of F protein and CCG-PS or PEG$_6$-CCG.

| Immunogen | sera GMT | | | | NW | | VW | |
|---|---|---|---|---|---|---|---|---|
| | IgG | IgG1 | IgG2a | IgA | IgG | IgA | IgG | IgA |
| F protein | 26,322 +/− 51,020 | 2,909 +/− 5,770 | <100 | <100 | <25 | <25 | <25 | <25 |
| F protein CCG-PS | 115,336 +/− 32,747 | 14,423 +/− 5,079 | 254 +/− 457 | <100 | <25 | <25 | 223 | 261 |
| F protein PEG$_6$-CCG | 111,761 +/− 108,591 | 9,218 +/− 7,565 | 626 +/− 665 | 381 +/− 50 | <25 | 103 | <25 | 443 |
| F protein A10H | 71,756 +/− 36,340 | 43,136 +/− 19,917 | 1,553 +/− 1,099 | <100 | <25 | <25 | 258 | <25 |
| RSV A2 | 79,236 +/− 32,310 | 5,962 +/− 5,251 | 20,819 +/− 7,258 | 752 +/− 50 | <25 | <25 | <25 | 594 |

Mice were bled on day 27 and individual mice were analyzed for serum antibody titers by ELISA. Similarly, pooled mucosal wash samples were taken on day 28 and analyzed for anti-F protein specific IgG and IgA. No IgA was detected in bronchoalveolar washes (BAW).
VW = vaginal wash,
NW = nasal wash.

Example X

Non-typeable *Haemophilus influenzae* (NTHi) Outer Membrane Protein (OMP) rP4

This experiment compared the mucosal adjuvant activities of CCG-PS and PEG$_6$-CCG for NTHi recombinant P4 protein following intranasal administration in BALB/c mice.

Vaccines were administered intranasally on days 0 and 21 in a total volume of 5 µl. Mice were bled on days 0, 21 and 28. Bronchoalveolar washes (BAW) and vaginal washes (VW) were performed and saliva samples collected on day 28.

Recombinant NTHi outer membrane P4 protein delivered in either CCG-PS or PEG$_6$-CCG significantly enhanced serum IgG antibody titers to recombinant P4 protein. There was no significant difference in serum IgA and IgG titers to recombinant P4 protein between the two delivery vehicles (P. 0.05 on day 28). Furthermore, 1 μg of recombinant P4 protein delivered in CCG-PS or PEG$_6$-CCG induced good titers of IgA antibodies to recombinant P4 in saliva and vaginal washes.

It appears that PEG$_6$-CCG was equivalent to CCG-PS in terms of specific serum antibody titers. However, it is noteworthy that only the PEG$_6$-CCG formulation induced a demonstrable rP4-specific nasal IgA antibody response.

TABLE 7

|  | Day 28 Anti-rP4 ELISA Titer | | | | |
| --- | --- | --- | --- | --- | --- |
| Immunogen | Serum IgG | Serum IgA | Nasal IgA | Saliva IgA | Vaginal IgA |
| NTHi rP4 in Saline | 207 | 79 | <10 | <10 | <10 |
| NTHi rP4 in 20% CCG-PS | 16,635 | 1295 | <10 | 128 | 125 |
| NTHi rP4 in PEG$_6$-CCG | 14,336 | 830 | 52 | 164 | 92 |

Furthermore, 1 μg of recombinant P4 protein delivered in CCG-PS or PEG$_6$-CCG significantly enhanced the numbers of responder mice as compared to that delivered in saline alone.

TABLE 8

| Mouse # | Saline | CCG-PS | PEG$_6$-CCG |
| --- | --- | --- | --- |
| 1 | 3,840 | 25,946 | 22,654 |
| 2 | 3,042 | 23,280 | 20,768 |
| 3 | 297 | 19,540 | 13,034 |
| 4 | 109 | 14,192 | 10,166 |
| 5 | 1 | 7,606 | 9,628 |
| Geometric mean ± SD | 207 ± 1,835 | 16,635 ± 7,346 | 14,336 ± 6,136 |

IgG response on day 28
Titers ranked from highest to lowest

Example XI

H. pylori rUrease

This experiment compared the mucosal adjuvant activities of CCG-PS and PEG$_6$-CCG on recombinant H pylori urease following intranasal administration in 10 μl volume in BALB/c mice.

Vaccines were administered on days 0 and 21. Mice were bled on days 0, 21 and 28. Bronchoalveolar washes (BAW) and vaginal washes (VW) were performed and saliva samples collected on day 28.

Recombinant H. pylori urease protein delivered in either PEG$_6$-CCG or CCG-PS vehicle significantly enhanced secondary serum IgG antibody titers to recombinant urease protein. There was no significant difference in serum IgG titers to recombinant urease protein. There was no significant difference in serum IgG titers to recombinant urease protein between the two delivery vehicles (P>0.05). However, 5 μg of recombinant urease protein delivered in CCG-PS and PEG$_6$-CCG did not induce detectable IgA antibodies to recombinant urease in any of the mucosal secretions analyzed in this experiment.

TABLE 9

| Immunogen | Serum IgG |
| --- | --- |
| H. pylori rUrease 5 μg in saline | <100 |
| H. pylori rUrease 5 μg in 20% CCG-PS | 64,787 ± 45,033 |
| H. pylori rUrease 5 μg in 5% PEG$_6$-CCG | 40,489 ± 28,674 |

Serum IgG anti-recombinant urease ELISA endpoint titers were determined on individual serum samples (5 per group) collected on day 28.

Example XII

N. meningitidis rPilin

In this example, the mucosal adjuvant activity of PEG$_6$-CCG was studied using recombinant N. meningitidis pilin as a vaccine antigen.

Groups of 5 BALB/c mice were immunized intranasally in 10 μl volume with 5 μg recombinant N. meningitidis pilin (rPilin) delivered in 20% CCG-PS, 5% PEG$_6$-CCG or in saline on days 0, 14 and 21 were bled on day 28. Bronchoalveolar washes (BAW), vaginal washes (VW) were performed and saliva samples collected on day 30.

A significant mucosal adjuvant effect is demonstrated when vaccine is administered IN in the PEG$_6$-CCG vehicle. With 5 μl g of rPilin delivered in PEG$_6$-CCG, sIgA in nasal and vaginal washes increased 16-and 32-fold in comparison to the saline control group on day 28. In contrast to PEG$_6$-CCG formulation, CCG-PS formulation showed only a 2-fold increase of sIgA titers in nasal washes and 11-fold increase in vaginal washes. These data suggested that PEG$_6$-CCG maybe an improved delivery vehicle for recombinant N. meningitidis pilin protein.

TABLE 10

| Immunogen | Serum IgA | Nasal IgA | Vaginal IgA |
| --- | --- | --- | --- |
| N. mening iPilin in saline | 6,168 | 12 | 15 |
| N. mening rPilin in 20% CCG-PS | 178,867 | 26 | 106 |
| N. mening rPilin in 5% PEG$_6$-CCG | 135,994 | 194 | 482 |

Example XIII

GC rPilin

In this example, the mucosal adjuvant activity of PEG$_6$-CCG was investigated using recombinant GC pilin as a vaccine antigen.

Groups of 5 BALB/c mice were immunized intranasally in 10 μl volume with 10 μg recombinant GC pilin (rpilin) with or without 5% PEG$_6$-CCG on days 0 and 14 and were bled on day 28. Vaginal washes were collected on day 29.

A significant adjuvant effect is demonstrated when vaccine is administered IN in the PEG$_6$-CCG vehicle. With 10 μg of rPilin delivered in PEG$_6$-CCG, serum anti-rPilin IgA and IgG antibody titers increased 2- and 5-fold on day 28, respectively. Whole cell ELISA titers also slightly increased (10,570 vs. 6,843). sIgA in vaginal washes increased more than 4-fold.

TABLE 11

| Immunogen | Serum IgA | Serum IgG | Whole Cell IgG | Vaginal wash IgA |
|---|---|---|---|---|
| rPilin in saline | 301 | 6,422 | 6,843 | 351 |
| rPilin in 5% PEG$_6$-CCG | 609 | 34,358 | 10,570 | 1,517 |

Nasal washes were not collected in this experiment.
CCG-PS was not included in this experiment.

Example XIV

Assessment of Acceptability and Tolerability of Mucosal Adjuvants

The acceptability and tolerability of two mucosal adjuvants (CCG-PS and PEG$_6$-CCG) were assessed in a clinical study. Twenty-nine healthy individuals (15 males and 14 females), 18 years old or older, were enrolled in the study.

The treatment consisted of five intranasal spray doses. The first two doses containing isotonic saline were unblinded to the investigator and the subjects. These two doses of saline were given simultaneously into both nostrils, serving as the comparison bases for the subjects and the investigator to evaluate the testing adjuvants. The other doses, containing saline (NS), CCG-PS (RV) and PEG$_6$-CCG (SG), were blinded to both the investigator and the subjects. The three testing doses were administered intranasally, each dose being separated by a thirty-minute interval, and administered according to the following regimen:

TABLE 12

| Nostril Sequence | Adjuvant Sequence (Dose 1 - Dose 2 - Dose 3) | # Subjects |
|---|---|---|
| right - left - right (RLR) | NS - RV - SG | 5 |
| | NS - SG - RV | 4 |
| | RV - SG - NS | 3 |
| | SG - RV - NS | 5 |
| left - right - left (LRL) | NS - RV - SG | 3 |
| | NS - SG - RV | 2 |
| | RV - SG - NS | 3 |
| | SG - RV - NS | 4 |

Both the investigator's and the subjects' evaluations of the adjuvants were collected. The investigator's evaluations were scored by the investigator for the nasal cavity thirty minutes after each dosing, and was an overall judgment of the redness, increased secretion and macroscopic side effects of the nasal cavity.

The subjects' evaluations were given by the subjects for irritability contrasting with the unblinded saline at 0, 5, 10, 20 and 30 minutes after each dosing of the adjuvants. The subjects also ranked the relative degree of irritation associated with each treatment.

The investigator's evaluation scores were summarized for each adjuvant. The irritability scores by the subjects were summarized at each time point for each adjuvant, and the subjects' evaluation scores at each time point were summed to represent the total irritability scored by the subjects. The statistical method was the Mantel-Haenszel Chi-square test (MH). The statistical significance level was 0.05 in the analysis.

Twenty-three subjects scored CCG-PS as "definitely much more irritating or uncomfortable than saline" immediately after dosing (Table 13). Within 20 minutes, the apparent irritation reduced to at most slightly or not irritating for 20 of the 23 subjects. The remaining 3 subjects still felt strong irritation 30 minutes after dosing. Meanwhile, the investigator reported a minor (⅔) or major (⅓) irritation associated with CCG-PS to these 3 subjects.

In contrast, twelve subjects (a statistically-significant difference from CCG-PS) scored PEG$_6$-CCG as "definitely much more irritating or uncomfortable than saline" immediately after dosing (Table 13). Within 5 minutes, the strong irritation was reduced to slightly irritating for 9 of the 12 subjects. The remaining 3 of the 12 subjects plus an additional subject felt strong irritation associated with PEG$_6$-CCG at the end of the 30 minute follow-up period after dosing.

The irritation scores were summed at each time point by adjuvant. CCG-PS was significantly more irritating than PEG$_6$-CCG at the 0 and 5 minute time points ($p \leq 0.01$, Table 13). The irritation scores for the two adjuvants were not statistically different at the later time points.

In a direct comparison of the irritation associated with all 3 of the blinded doses received (i.e., compared to each other, not by comparison to saline), CCG-PS was the most irritating adjuvant. CCG-PS was the most irritating adjuvant according to 76% of the subjects (22/29).

TABLE 13

| | Acceptability - Subjects' Evaluation | | | | | | | | | | | |
|---|---|---|---|---|---|---|---|---|---|---|---|---|
| Differ- | Saline | | | | CCG-PS | | | | Softigen | | | |
| ence | 0 | 1 | 2 | sum | 0 | 1 | 2 | sum | 0 | 1 | 2 | sum |
| All | | | | | | | | | | | | |
| Min. | | | | | | | | | | | | |
| 0 | 26 | 3 | | 3 | 1 | 5 | 23 | 51 | 1 | 16 | 12 | 40 |
| 5 | 28 | 1 | | 1 | 2 | 13 | 14 | 41 | 7 | 20 | 2 | 24 |
| 10 | 28 | 1 | | 1 | 9 | 13 | 7 | 27 | 9 | 18 | 2 | 22 |
| 20 | 28 | 1 | | 1 | 19 | 7 | 3 | 13 | 12 | 14 | 3 | 20 |
| 30 | 28 | | | | 22 | 4 | 3 | 10 | 17 | 8 | 4 | 16 |

Note:
Difference code comparing to saline:
0 = not different;
1 = slightly different;
2 = very different.
Note:
RS = receiving CCG-PS first then Softigen;
SR = receiving PEG$_6$-CCG first then CCG-PS.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A composition comprising:

i) an adjuvant containing 0.01–70% v/v of glycerides selected from the group consisting of monoglycerides, diglycerides, and mixtures thereof, said glycerides having the formula (I):

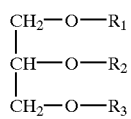

wherein $R_1$, $R_2$, and $R_3$ are independently selected from the group consisting of saturated or unsaturated $C_{6-24}$ fatty acids, water soluble polymers, and mixtures thereof, provided that the glyceride contains at least one water soluble polymer;

ii) at least one antigen; and iii) a physiologically acceptable aqueous vehicle.

2. A composition according to claim 1, wherein the water soluble polymers consist of $PEG_{2-30}$ residues of polyoxyethylene, or derivatives thereof, having 2–30 polyoxyethylene units.

3. A composition according to claim 1, wherein the v/v-% ratio of monoglycerides to diglycerides is from about 0.1:99.9 to about 99.9:0.1.

4. A composition according to claim 1, wherein the water soluble polymer is a $PEG_{3-6}$ residue of polyoxyethylene having 3 to 6 polyoxyethylene units.

5. A composition according to claim 4, wherein the glycerides have a structure selected from the group consisting of:

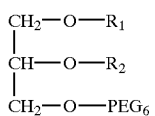

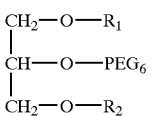

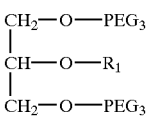

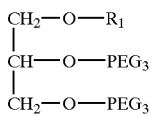

and the mixtures of II–V.

6. A composition according to claim 1, wherein $R_1$, $R_2$, and $R_3$ are selected from saturated $C_{6-14}$ fatty acids.

7. A composition according to claim 6, wherein R1, R2 and R3 are selected from saturated $C_{8-10}$ fatty acids.

8. A composition according to claim 1, wherein the glycerides have a concentration of from about 0.1% to about 99%.

9. A composition according to claim 1, wherein chiral carbons in the glyceride are either S- or R-form.

10. A composition according to claim 1, wherein the antigen is in a particulate form.

11. A composition according to claim 1, wherein the antigen is in a dissolved form.

12. A composition according to claim 1, further comprising one or more components selected from the group consisting of: surfactants, absorption promoters, water absorbing polymers, substances which inhibit enzymatic degradation, alcohols, organic solvents, oils, pH-controlling agents, solubilizers, stabilizers, HLB-controlling agents, viscosity controlling agents, preservatives, osmotic pressure controlling agents, propellants, air displacement, water, and mixtures thereof.

13. A composition according to claim 1 which is an immunogenic composition.

14. A composition according to claim 1 which is a vaccine composition.

15. A composition according to claim 1, wherein the antigen is selected from the group consisting of tetanus toxoid, hemagglutinin molecules from influenza virus, diphtheria toxoid, HIV gp120, IgA protease, insulin peptide B, *Spongospora subterranea* antigen, vibriose antigens, Salmonella antigens, pneumococcus antigens, respiratory syncytial virus antigens, *Haemophilus influenza* outer membrane proteins, *Helicobacter pylori* urease, *Neisseria meningitidis* pilins and *N. gonorrhoeae* pilins.

16. A composition according to claim 4, wherein the v/v-% ratio of monoglycerides to diglycerides is from about 5:95 to about 95:5.

17. A composition according to claim 8, wherein the glycerides have a concentration of about 0.5 to about 20% by weight.

18. A composition according to claim 1, wherein (i) is a monoglyceride and diglyceride mixture of caprylic and capric acid containing 3 to 6 polyoxyethylene units.

19. A nasal formulation suitable for delivery to the nasal mucosa, comprising:

i) an adjuvant containing 0.01–70% v/v of glycerides selected from the group consisting of monoglycerides, diglycerides, and mixtures thereof, said glycerides having the formula (I):

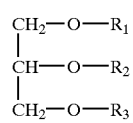

wherein $R_1$, $R_2$, and $R_3$ are independently selected from the group consisting of saturated or unsaturated $C_{6-24}$ fatty acids, water soluble polymers, and mixtures thereof, provided that the glyceride contains at least one water soluble polymer;

ii) at least one antigen; and iii) a physiologically acceptable aqueous vehicle in the form of a nasal spray or nasal aerosol.

20. The nasal formulation of claim 19, wherein (i) is a monoglyceride and diglyceride mixture of caprylic and capric acid containing 3 to 6 polyoxyethylene units.

21. The nasal formulation of claim 19, wherein (iii) is isotonic saline.

22. A composition, comprising:

i) an adjuvant containing 0.01–70% v/v of glycerides selected from the group consisting of monoglycerides, diglycerides, and mixtures thereof, said glycerides having the formula (I):

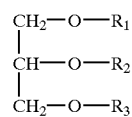

(I)

wherein $R_1$, $R_2$, and $R_3$ are independently selected from the group consisting of saturated or unsaturated $C_{6-24}$ fatty acids, water soluble polymers, and mixtures thereof, provided that the glyceride contains at least one water soluble polymer and provided that one of the groups $R_1$, $R_2$ and $R_3$ is replaced by bound antigen; and ii) a physiologically acceptable aqueous vehicle.

23. A composition, comprising:

i) an adjuvant containing 0.01–70% v/v of a monoglyceride and diglyceride mixture of caprylic and capric acid containing polyoxyethylene units;

ii) at least one antigen of a pathogenic microorganism; and iii) a physiologically acceptable aqueous vehicle.

24. A composition according to claim 23, wherein the antigen is selected from the group consisting of tetanus toxoid, hemagglutinin molecules from influenza virus, diphtheria toxoid, HIV gp120, IgA protease, insulin peptide B, *Spongospora subterranea* antigen, vibriose antigens, Salmonella antigens, pneumococcus antigens, respiratory syncytial virus antigens, *Haemophilus influenza* outer membrane proteins, *Helicobacter pylori* urease, *Neisseria meningitidis* pilins and *N. gonorrhoeae* pilins.

25. A composition according to claim 23, wherein the adjuvant contains three to six polyoxyethylene units.

26. A composition, comprising:

i) an adjuvant containing 0.01–70% v/v of glycerides selected from the group consisting of monoglycerides, diglycerides, and mixtures thereof, said glycerides having the formula (I):

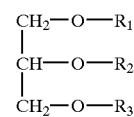

(I)

wherein $R_1$, $R_2$, and $R_3$ are independently selected from the group consisting of saturated or unsaturated $C_{6-24}$ fatty acids, water soluble polymers, and mixtures thereof, provided that the glyceride contains at least one water soluble polymer;

ii) at least one antigen of a pathogenic microorganism; and iii) a physiologically acceptable aqueous vehicle.

27. A composition according to claim 17, wherein the glycerides have a concentration of about 1 to about 15% by weight.

28. A composition comprising:

i) an adjuvant containing 0.01–70% v/v of glycerides selected from the group consisting of monoglycerides, diglycerides, and mixtures thereof, wherein the v/v % ratio of monoglycerides to diglycerides is from about 5:95 to about 95:5, said glycerides having the formula (I):

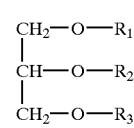

(I)

wherein $R_1$, $R_2$, and $R_3$ are independently selected from the group consisting of saturated or unsaturated $C_{6-24}$ fatty acids, water soluble polymers, and mixtures thereof, provided that the glyceride contains at least one water soluble polymer;

ii) at least one antigen; and iii) a physiologically acceptable aqueous vehicle.

* * * * *